United States Patent
Bjork et al.

(10) Patent No.: US 7,297,107 B1
(45) Date of Patent: Nov. 20, 2007

(54) FULCRUM WEDGE CLAMP

(75) Inventors: Todd M. Bjork, River Falls, WI (US); Todd W. Sharratt, Birchwood, MN (US); Christopher Lee Berg, Crystal, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 0 days.

(21) Appl. No.: 10/732,491

(22) Filed: Dec. 10, 2003

Related U.S. Application Data (63) Continuation of application No. 10/664,195, filed on Sep. 17, 2003.

(51) Int. Cl.
*A61B 1/32* (2006.01)

(52) U.S. Cl. .................................... 600/227

(58) Field of Classification Search ................ 600/184, 600/201, 226, 227; 403/110, 350, 373, 374.1, 403/374.2; 248/291.1, 292.12, 231.61
See application file for complete search history.

(56) References Cited

U.S. PATENT DOCUMENTS

| | | | | |
|---|---|---|---|---|
| 4,949,707 A | * | 8/1990 | LeVahn et al. ............. | 600/234 |
| 5,224,680 A | * | 7/1993 | Greenstein et al. ...... | 248/316.4 |
| 5,727,899 A | * | 3/1998 | Dobrovolny ................. | 403/389 |
| 5,752,954 A | * | 5/1998 | Mata et al. ................... | 606/59 |
| 6,033,363 A | * | 3/2000 | Farley et al. ............... | 600/234 |
| 6,042,540 A | | 3/2000 | Johnston et al. ............ | 600/213 |
| 6,736,775 B2 | | 5/2004 | Phillips ...................... | 600/234 |
| 2002/0177754 A1 | | 11/2002 | Phillips ...................... | 600/234 |
| 2003/0120132 A1 | | 6/2003 | Phillips ...................... | 600/210 |
| 2003/0191370 A1 | | 10/2003 | Phillips ...................... | 600/201 |

* cited by examiner

*Primary Examiner*—Anuradha Ramana
(74) *Attorney, Agent, or Firm*—Westman, Champlin & Kelly, P.A.

(57) ABSTRACT

A surgical joint includes a first clamping member comprising a first clamping surface for engaging a first surgical rod and an attachment end. A second clamping member is mounted with respect to the first clamping member wherein the second clamping member comprises a second clamping surface for engaging a second surgical rod. A shaft is disposed through and positioned within the attachment end of the first clamping member and wherein the shaft is in communication with the second clamping member. A force providing mechanism is disposed between the first and second clamping members and disposed about the shaft wherein when the force providing mechanism and the shaft are movable with respect to each other and place the first and second clamping members in either a non-clamping position or a clamping position.

4 Claims, 9 Drawing Sheets

FULCRUM WEDGE CLAMP

CROSS-REFERENCE TO RELATED APPLICATION(S)

This is a Continuation of application Ser. No. 10/664,195, filed Sep. 17, 2003.

BACKGROUND OF THE INVENTION

The present invention relates generally to a captivated clamp for use in mounting surgical retractors with respect to an operating table. More particularly, the present invention relates to a clamp that is positioned into a clamping position with a wedge.

Prior to performing a surgical procedure requiring retraction, a retractor support apparatus is typically disposed about the surgical site. Retractor clamps are commonly used to mount the retractor support apparatus with respect to an operating table. Retractor clamps are also used to attach surgical retractors to the retractor support apparatus. Some retractor clamps are manufactured in a captivated configuration so that users cannot disassemble the retractor clamp.

A retractor clamp typically includes a first clamping member, a second clamping member and a handle. A typical configuration for a clamping member is to have the clamping member fabricated from a unitary structure that is generally in the shape of the letter "U". In each of the retractor clamps, the object to be clamped is placed between the legs of the U-shaped structure so that the object is proximate the base of the U-shaped structure. Movement of the legs of the U-shaped structure towards each other causes the object to be clamped with respect to the clamping member.

The use of clamping members having U-shaped structures has some disadvantages in particular surgical procedures. First, the U-shaped structure must be disposed over an end of a retractor support apparatus and slid into a desired position. When previously placed retractor clamps are disposed between the end of the support arm and the desired location, the interfering clamps must be removed to allow the additional surgical clamp to be disposed in the desired location. Having to disassemble at least a portion of the surgical support apparatus about a surgical site to add additional retractors adds unnecessary additional time and expense to the surgical procedure.

Additionally, the second U-shaped structure and the handle are typically disposed above the first U-shaped structure and the retractor support arm. Because the second U-shaped structure and the handle are located above the surgical support arm, the second U-shaped structure and the handle may obstruct access to the surgical site during some surgical procedures.

SUMMARY OF THE INVENTION

The present invention includes a surgical joint having a first clamping member comprising a first clamping surface for engaging a first surgical rod and an attachment end. A second clamping member is mounted with respect to the first clamping member where the second clamping member comprises a second clamping surface for engaging a second surgical rod. A shaft is disposed through and positioned within the attachment end of the first clamping member where the shaft is in communication with the second clamping member. A force providing mechanism is disposed between the first and second clamping members and disposed about the shaft where the force providing mechanism and the shaft are movable with respect to each other and place the first and second clamping members in either a non-clamping position or a clamping position.

DETAILED DESCRIPTION OF THE PREFERRED EMBODIMENTS

Figure 1:
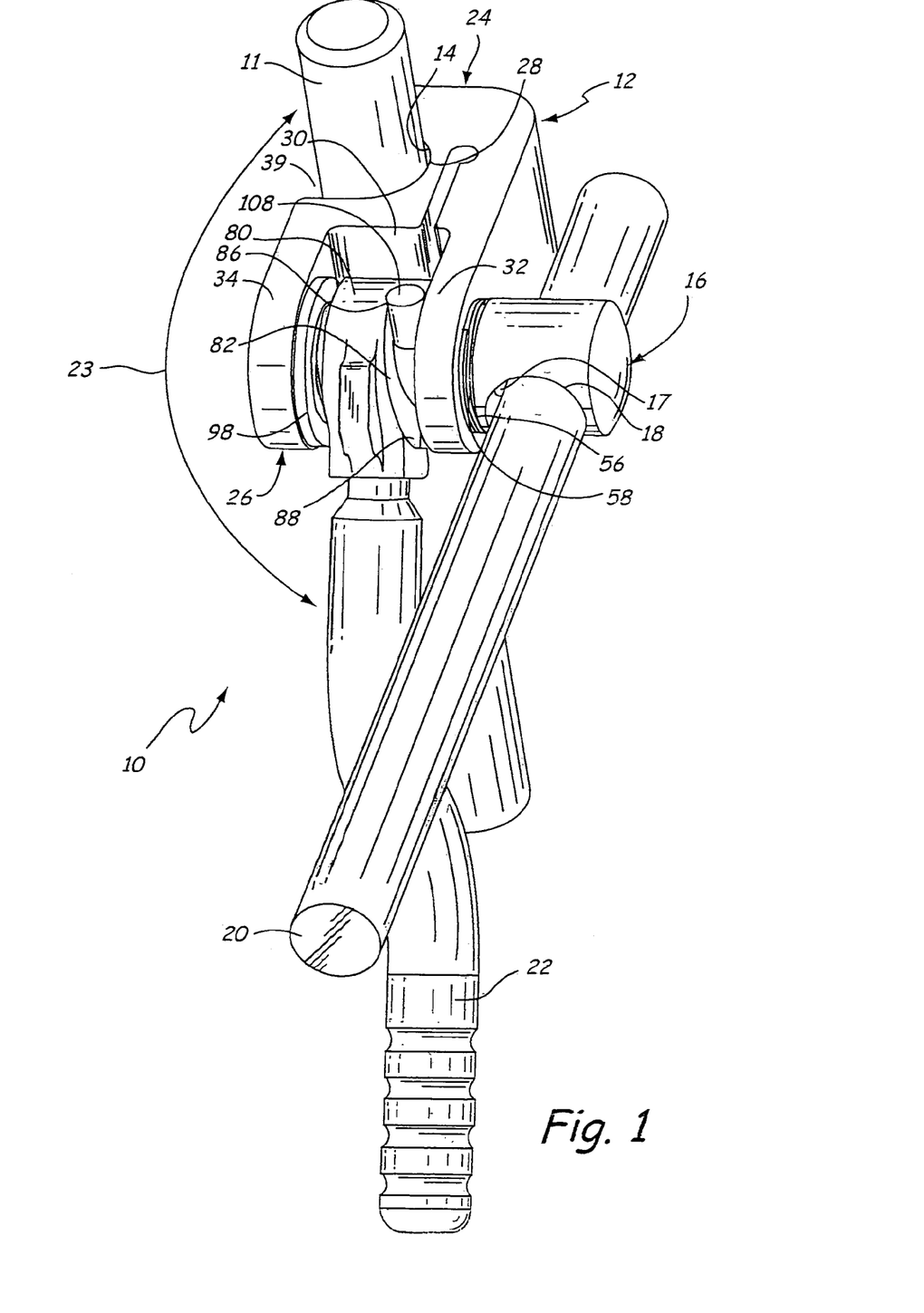
FIG. 1 is a perspective view of the surgical clamp of the present invention in a non-clamping position.

The present invention includes a low profile surgical clamp generally illustrated in FIG. 1 at 10. The clamp 10 is particularly suited for mounting a retractor (not shown) with respect to an operating table (not shown). The clamp 10 includes a first clamping member 12 having a first clamping surface 14 and a second clamping member 16 having a second clamping surface 18. Other components may be substituted for the second clamping member 16 such as, but not limited to, permanently attached retractors, or retractors that are attached using other types of clamps or fasteners.

To position the clamp 10 within the surgical site, a clamping end 24 of the first clamping member 12 is positioned proximate a retractor support arm 11. The first clamping surface 14 proximate the clamping end 24 is disposed about the portion of the retractor support arm 11.

The first clamping member 12 also includes an attachment end 26 and a fulcrum portion 28 between the clamping end 24 and the attachment end 26. The first clamping member 12 has a recess 30 defined by an upper leg portion 32 and a lower leg portion 34 proximate the attachment end 26.

Figure 3:
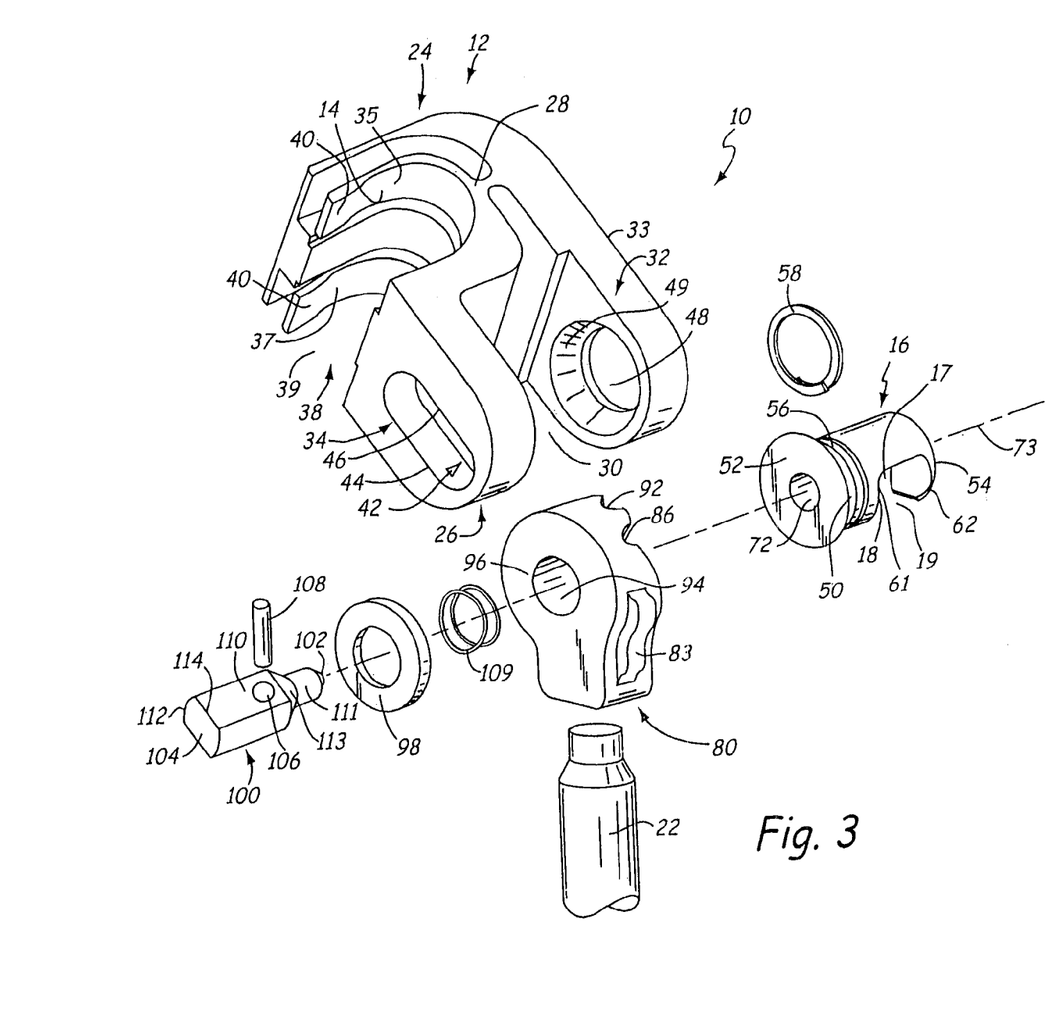
FIG. 3 is an exploded view of the surgical clamp of the present invention.

The fulcrum portion 28 extends between the upper leg portion 32 and the lower leg portion 34 as best illustrated in FIG. 3. The fulcrum portion 28 allows the upper leg portion 32 to move with respect to the lower leg portion 34 so that the retractor support arm 11 may be clamped within the first clamping surface 14.

Figure 2:
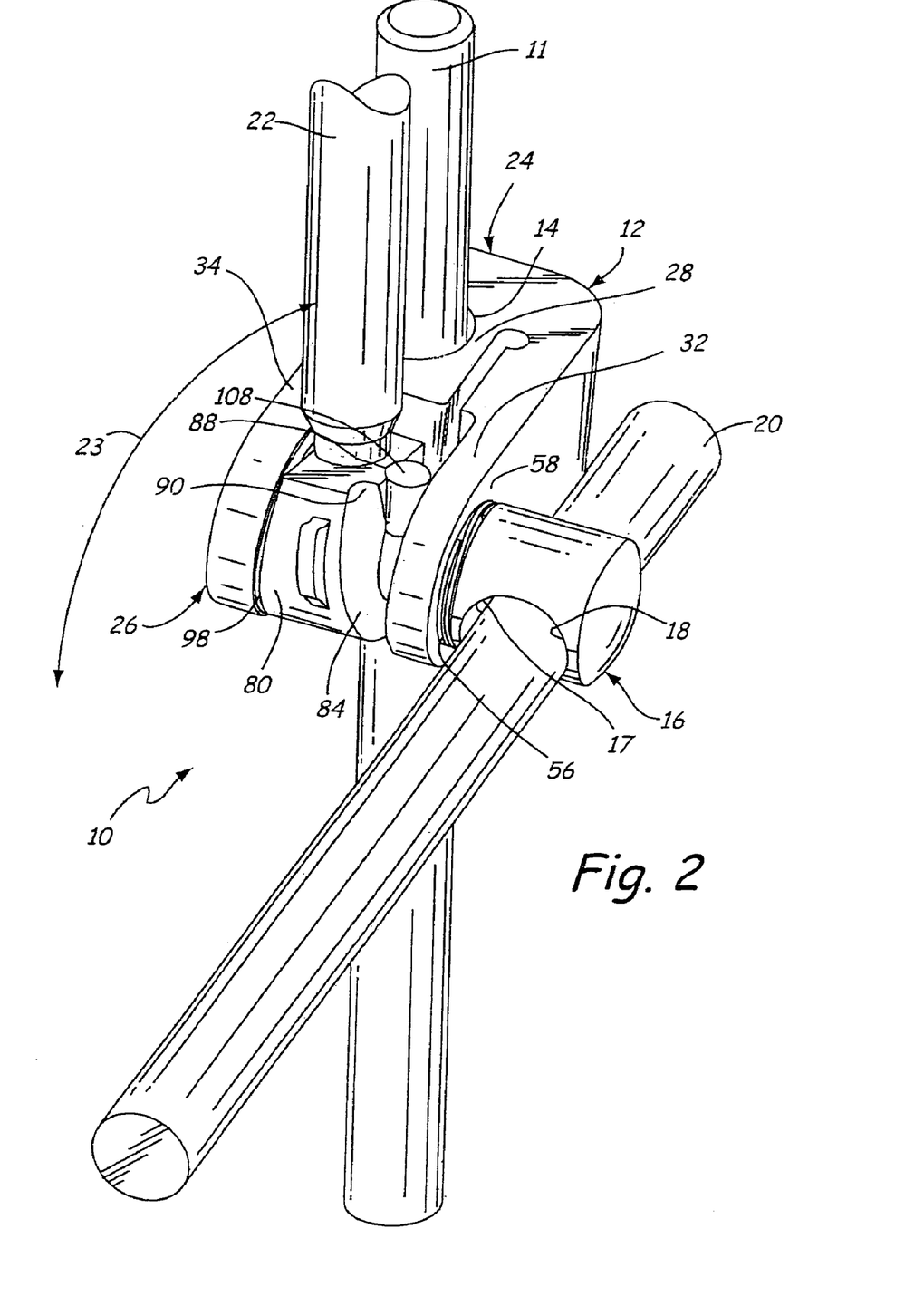
FIG. 2 is a perspective view of the surgical clamp of the present invention in a clamping position.

An actuating mechanism 80 is disposed within the recess 30 between the upper leg portion 32 and the lower leg portion 34 of the first clamping member 12 as illustrated in FIGS. 1 and 2. The actuating mechanism 80 preferably is a wedge. By the term wedge is meant a component that progressively increases in cross-sectional thickness such that when the wedge is moved or rotated in a restricted space, the movement or rotation of the wedge causes progressive increase in thickness to cause a force to be applied, such as a leverage action, to spread apart leg portions of the clamp. The wedge may take on forms other than those specifically described herein.

The wedge 80 is movable within the recess 30 and forces the upper and lower leg portions 32, 34 apart and causes the fulcrum portion 28 to flex. As the fulcrum portion 18 flexes, the first clamping member 12 constricts. When constricted, the first clamping surface 14 frictionally engages the retractor support arm 11 in a clamped relationship.

The first clamping surface 14 is configured to generally conform to the cross-sectional configuration of the retractor support arm 11, but may be configured to conform to other shaped cross-sections. In a preferred embodiment, the first clamping surface 14 conforms to a substantially circular cross-sectional configuration of the retractor support arm 11.

Referring to FIG. 3, the first clamping surface 14 defines a clamping slot 38 that permits the first clamping member 12 to be placed on the retractor support arm 11 without moving any other surgical equipment that has been previously disposed upon the retractor support arm 11. When the clamp 10 is in a non-clamping position, the first clamping member 12 is retained upon the retractor support arm 11 by a constricted entrance 39 to the clamping slot 38. In an exemplary embodiment, a bead or raised surface 40 is disposed along a length of resilient portions 35, 37 that move as the retractor support arm 11 is positioned within the clamping slot 38 where the bead 40 constricts the entrance 39. However other devices that constrict the entrance 39 to the clamping slot 38 are within the scope of the present invention including, but not limited to, a clip, a roller or a spring loaded device.

The constricted entrance 39 provides a preliminary clamping force around the portion of the retractor support arm 11 such that the constricted entrance 39 to the clamping slot 38 prevents the clamp 10 from slipping off the retractor support arm 11 when the clamp 10 is in non-clamping position. The entrance 39 of the clamping slot 38 should not be so constricted to prevent use of manual force to position the first clamping member 12 about the portion of the retractor support arm 11. However, the entrance 39 of the clamping slot 38 should be sufficiently constricted to prevent the first clamping member 12 from accidentally slipping off of the retractor support arm 11. An exemplary amount of constriction of the entrance 39 of the clamping slot 38 is between about 0.010 inches and 0.020 inches and preferably about 0.015 inches.

The second clamping member 16 extends through a through bore 48 defined by a frusto-conical surface 49 within the upper leg portion 32 of the first clamping member 12. The second clamping member 16 includes a frusto-conical surface 50 at a proximal end 52 that cooperates with the frusto-conical surface 49.

With the second clamping member 16 being positioned within the upper leg portion 32, an annular groove 56 on the second clamping member 16 is positioned above an upper surface 33 of the upper leg portion 32. A snap ring 58 is disposed within the annular groove 56 and rotatably captivates the second clamping member 16 within the upper leg portion 32 of the first clamping member 12 as illustrated in FIGS. 1 and 2.

Referring to FIGS. 1-3, the second clamping surface 18 is positioned on a distal end portion 54. A retractor handle 20 is disposed within an opening 17 defined by the second clamping surface 18. An arcuate upper portion 62 and an end 102 of the shaft 100 constrict an entrance 19 of the opening 17 and retain the retractor handle 20 within the second clamping surface 18. Although the second clamping member 16 is described and illustrated in the drawings as retaining and clamping a retractor handle 20, the second clamping member 16 can also retain and clamp other surgical devices. By surgical devices is meant any element that is useful in conducting a surgical procedure including, but not limited to, a retractor support apparatus, a retractor or any other medical instrument that is used during a surgical procedure such as a camera, a light or a catheter.

The second clamping member 16 is positioned into a clamping position at approximately the same time that the wedge 80 forces the first and second leg portions 32, 34 apart. When the second clamping member 16 is in the clamping position, the second clamping member 16 is non-rotatably fixed with respect to the first clamping member 12 and the retractor handle 20 is frictionally engaged within the second clamping surface 18.

In the clamping position, the second clamping member 16 is rotatably fixed within the upper leg portion 32 by a frictional engagement of the cooperating frusto-conical surfaces 49, 50. The retractor handle 20 is frictionally engaged between the arcuate upper portion 62 and an end 102 of a shaft 100 positioned through a through bore 72. The through bore 72 extends through the second clamping member 16 along an axis 73 and intersects a bottom portion 61 of the clamping surface 18.

Referring to FIG. 3, an upper substantially circular cross-section portion 111 of a shaft 100 extends through an elongated slot 42 within the lower leg portion 34, a washer 98, a compression spring 109, a through bore 94 of the wedge 80, the through bore 48 of the upper leg portion 32 and into the through bore 72 of the second clamping member 16. The end 102 of the upper portion 111 extends into the opening 17.

A lower portion 110 of the shaft 100 captivates the washer 98 and the compression spring 109 between the lower leg portion 34 and the wedge 80. With the shaft 100 disposed within the clamp 10, a shoulder 113 is positioned proximate the proximal end 52 of the second clamping member 16. The shoulder 113 cooperates with the proximal end 52 to prevent the shaft 100 from being further inserted into the clamp 10.

Referring to FIGS. 1-3, the washer 98 is positioned between a bottom surface 96 of the wedge 80 and the lower leg portion 34. The washer 98 prevents wear of the lower leg portion 34 and the wedge 80 as the clamp 10 is used over time.

The lower portion 110 of the shaft 100 has substantially flat, parallel sides 112, 114, respectively, that cooperate with substantially flat, parallel sides 44, 46, respectively, of the elongated slot 42. The cooperation of the lower portion 110 within the elongated slot 42 prevents rotation of the shaft 100 within the clamp 10 while allowing the shaft 100 to move slightly with respect to the first and second clamping members 12, 16.

The shaft includes a bore 106 that is in a substantially perpendicular relationship with the axis 73. With the lower portion 110 of the shaft 100 positioned within the elongated slot 42, the bore 106 is positioned between the proximal end 52 of the second clamping member 16 and the wedge 80. A pin 108 is positioned through the bore 106 in the shaft 100.

The compression spring 109 biases the wedge 80 toward the second clamping member 16 such that first and second ramped surfaces 82, 84, respectively, of the wedge 80 engage the pin 108. The engagement of the pin 108 with the first and second ramped surfaces 82, 84, respectively, of the wedge 80 prevents the shaft 100 from exiting from the lower leg portion 34. The compression spring 109 also biases the end 102 of the shaft 100 into the opening 17 by forcing the shoulder 113 into the proximal end 52 of the second clamping member 16

Figure 4:
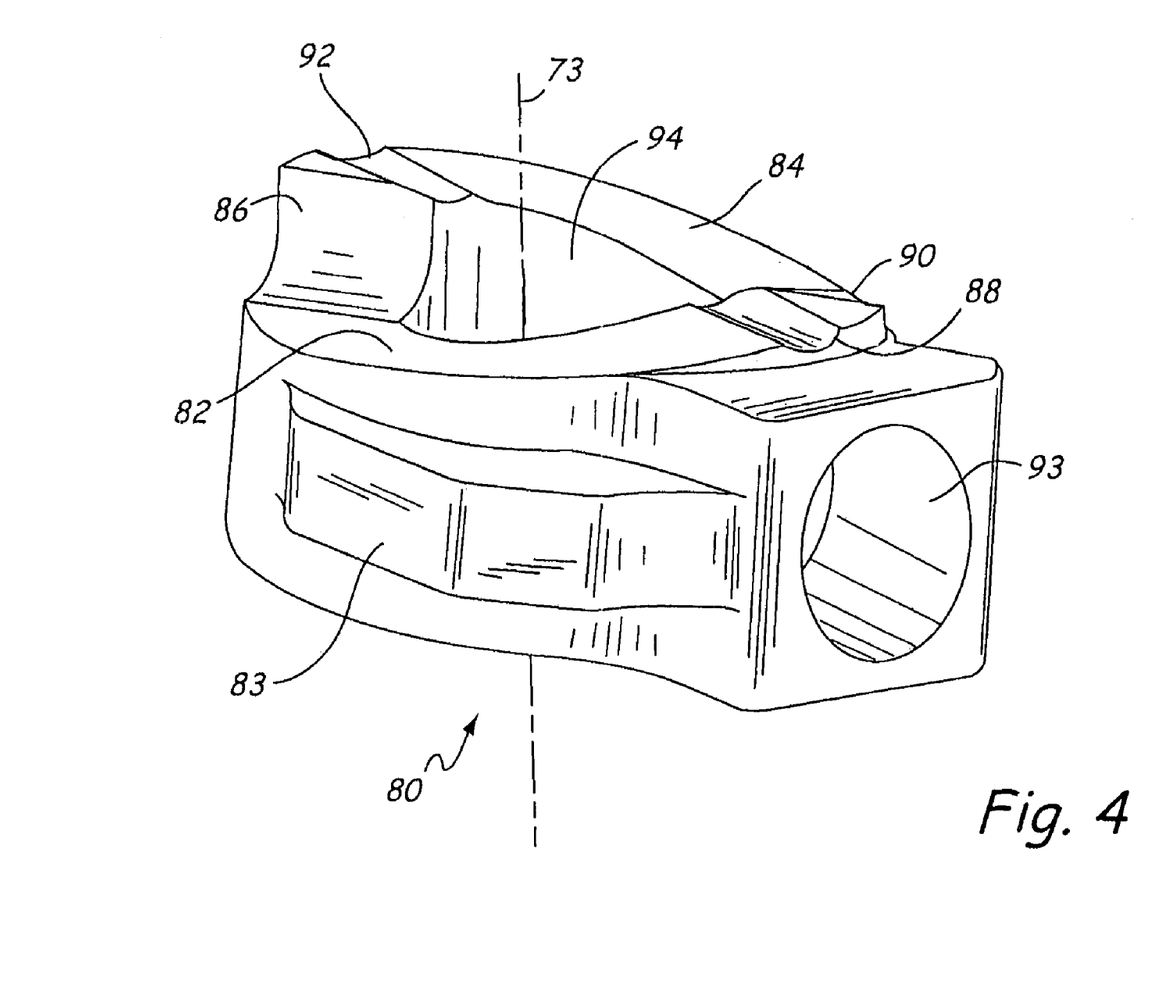
FIG. 4 is a perspective view of an actuating mechanism of the surgical clamp of the present invention.
Figure 5:
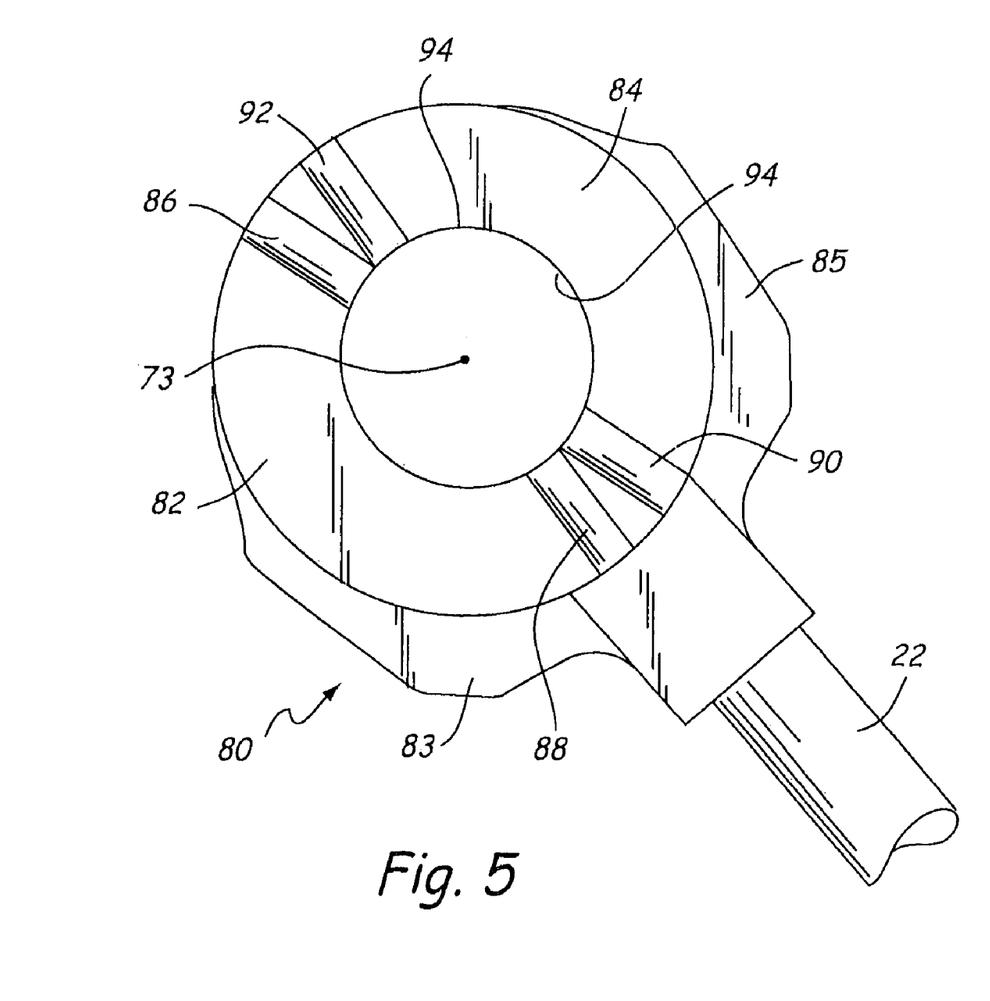
FIG. 5 is a top view of the actuating mechanism of the surgical clamp of the present invention.

Referring to FIGS. 4 and 5, the wedge 80 includes the first and second ramped surfaces 82, 84, respectively, that are symmetric about the axis 73. Arcuate indentions 86, 90 are located each at a base of the first and second ramped surfaces 82, 84, respectively, and opposite each other. Arcuate indentions 88, 92 are located each at an apex of the first and second ramped surfaces 82, 84, respectively, and opposite each other.

The pin 108 engages the arcuate indentions 86, 90 each at the base of the first and second ramped surfaces 82, 84, respectively, to retain the wedge 80 in a first position where the first and second clamping members 12, 16, respectively are in non-clamping positions. The pin 108 engages the arcuate indentions 88, 92 each at the apex of the first and second ramped surfaces 82, 84, respectively, to retain the wedge 80 in a second position where the first and second clamping member 12, 16, respectively, are in clamping positions.

In operation, the wedge 80 is positioned in the first position when the pin 108 is engaged with the arcuate indentions 86, 90 each at the base of the first and second ramped surfaces 82, 84, respectively, as best illustrated in FIG. 1. With the wedge 80 in the first position, the first clamping member 12 and the second clamping member 16 can accept the retractor support arm 11 and the retractor handle 20, respectively, and the second clamping member 16 is rotatable with respect to the first clamping member 12.

The first clamping member 12 is disposed in a selected position on the retractor support arm 11 by positioning the constricted entrance 39 of the clamping slot 38 proximate the retractor support arm 11. Manual force is applied to the first clamping member 12 substantially perpendicular to an axis of the retractor support arm 11 to overcome the constricted entrance 39 of the clamping slot 38, thereby disposing the first clamping member 12 about the retractor support arm 11. With the wedge 80 in the first position, the first clamping member 12 is slidably positionable on the retractor support arm 11.

With the first clamping member 12 positioned on the retractor support arm 11, the retractor handle 20 is positioned proximate the constricted entrance 19 of the opening 17 within the second clamping member 16. Manual force is applied substantially perpendicular to an axis of the retractor handle 20 to overcome the bias of the compression spring 109 and force the end 102 of the shaft 100 from the opening 17 and dispose the retractor handle 20 within the opening 17. With the retractor handle 20 positioned within the opening 17, the end 102 of the shaft 100 is biased back into the opening 17 such that the retractor handle 20 is slidably retained within the second clamping member 16.

To position the wedge 80 into the second or clamping position, a handle 22 fixedly attached to the wedge 80 is moved in the direction of arrows 23 as illustrated in FIG. 1, which rotates the wedge 80 about the shaft 100 and axis 73. Although the preferred embodiment includes a rotatable wedge, one skilled in the art will recognize that moving a wedge in other manners such as sliding is also within the scope of the invention. The purpose of the wedge 80 is to increase the wedge's thickness within the recess 30 to force the upper and lower leg portions 32, 34, respectively, apart.

As the wedge 80 is rotated about the shaft 100, the pin 108 moves along the first and second ramped surfaces 82, 84 toward the apexes of the first and second ramped surfaces 82, 84, respectively. As the pin 108 rises on the first and second ramped surfaces, 82, 84, respectively, an increasing force is placed upon the pin 108. A maximum force is placed upon the pin 108 when the wedge 80 is positioned into the second position when the pin 108 is disposed within the arcuate indentions 88, 92 each at the apex of the first and second ramped surfaces 82, 84, respectively, as best illustrated in FIG. 2. The wedge 80 includes first and second strengthening portions 83, 85 to stiffen the wedge 80 and prevent the wedge 80 from flexing as the wedge 80 is rotated, as best illustrated in FIGS. 1-5.

Referring to FIGS. 1 and 2, as the wedge 80 is rotated from the first position to the second position, the wedge 80 compresses the compression spring 109, and the distance between the pin 108 and the washer 72 becomes less than the height of the wedge 80. With the wedge 80 in the second position, the height of the wedge 80 is greater than the distance between the pin 108 and the washer 72, such that the wedge 80 forces the first and second leg portions 32, 34 apart by forcing the shoulder 113 of the shaft into the proximal end 52 of the second clamping member 16 and transferring the force to the first leg portion 32. With the first and second leg portions 32, 34 forced apart, the fulcrum portion 28 flexes which causes the first clamping slot 38 to constrict such that the first clamping surface 14 frictionally engages the retractor support arm 11.

With the wedge 80 in the second position, the shoulder 113 is forced upward and into the proximal end 52 of the second clamping member 16 and creates a frictional engagement between the cooperating frusto-conical surface 49 of the through bore 48 in the upper leg portion 32 and the frusto-conical surface 50 of the second clamping member 16. The frictional engagement of the frusto-conical surfaces 49, 50 prevents rotational movement of the second clamping member 16 with respect to the first clamping member 12.

With the wedge 80 in the second position, the end 102 of the shaft 100 is raised into the opening 17 through the through bore 72. The raised end 102 of the shaft 100 contacts the retractor handle 20 and creates a frictional engagement between the arcuate upper portion 62 of the second clamping surface 18, the retractor handle 20 and the end 102 of the shaft 100.

One skilled in the art will recognize that a plane of movement of the handle 22 approximately intersects an axis of the retractor support arm 11 as best illustrated in FIGS. 1 and 2. Therefore, the operator can conveniently manipulate the wedge 80 from the first position to the second position by gripping the handle 22 and the retractor support arm 11 with one hand and forcing the handle 22 toward the retractor support arm 11.

The surgical clamp 10 of the present invention also provides a low profile clamping device for conducting the surgical procedure. What is meant by low profile is that the second clamping member 16 and a handle 22 are disposed proximate the retractor support arm 11 as best illustrated in FIGS. 1 and 2. By disposing the second clamping member 16 and the handle 22 proximate the retractor support arm 11, the surgical site remains relatively open and free of obstruction thereby providing better access to the surgical site.

An advantage of the clamp 10 of the present invention is that the clamp 10 does not have to be slid along the retractor support arm 11 to a new selected position. The retractor clamp 10 can be repositioned on the support arm 11 by first positioning the wedge 80 into the first position such that the first clamping slot 38 is not constricted and detaching the first clamping member 12 from the retractor support arm 11. The first clamping member 12 is detachable from the retractor support arm 11 by applying manual force in an opposite direction as used to position the first clamping member 12 on the support arm 11. After the clamp 10 has been removed from the retractor support arm 11, the clamp 10 is repositionable on the retractor support arm 11 by positioning an entrance 39 to the clamping slot 38 against the retractor support arm 11 and applying manual force substantially perpendicular to the axis of that portion of the retractor support arm 11.

The retractor handle 20 can also be repositioned within the second clamping member 16 without having to slide the retractor handle 20 with respect to the second clamping surface 18. The retractor handle 20 is removed from the second clamping member 16 by providing manual force in the opposite direction of the force used to position the retractor handle 20 within the opening 17 of the second clamping member 16. The retractor handle 20 can be reinserted into the opening 17 by reapplying manual force generally perpendicular to the axis of the retractor handle 20.

The surgical clamp 10 of the present invention, having the first and second clamping surfaces 14, 18, respectively, enables the clamp 10 to be positioned upon the retractor support arm 11 in a selected position. Further, an additional retractor can be easily and conveniently positioned within a surgical site without having to dispose the end of the retractor through the opening 17 defined by the second clamping surface 18. The convenience of the surgical clamp 10 of the present invention allows the surgical site to be quickly assembled, modified during a surgical procedure, and disassembled, which enables a surgical team to conduct a more efficient surgical procedure.

Figure 6:
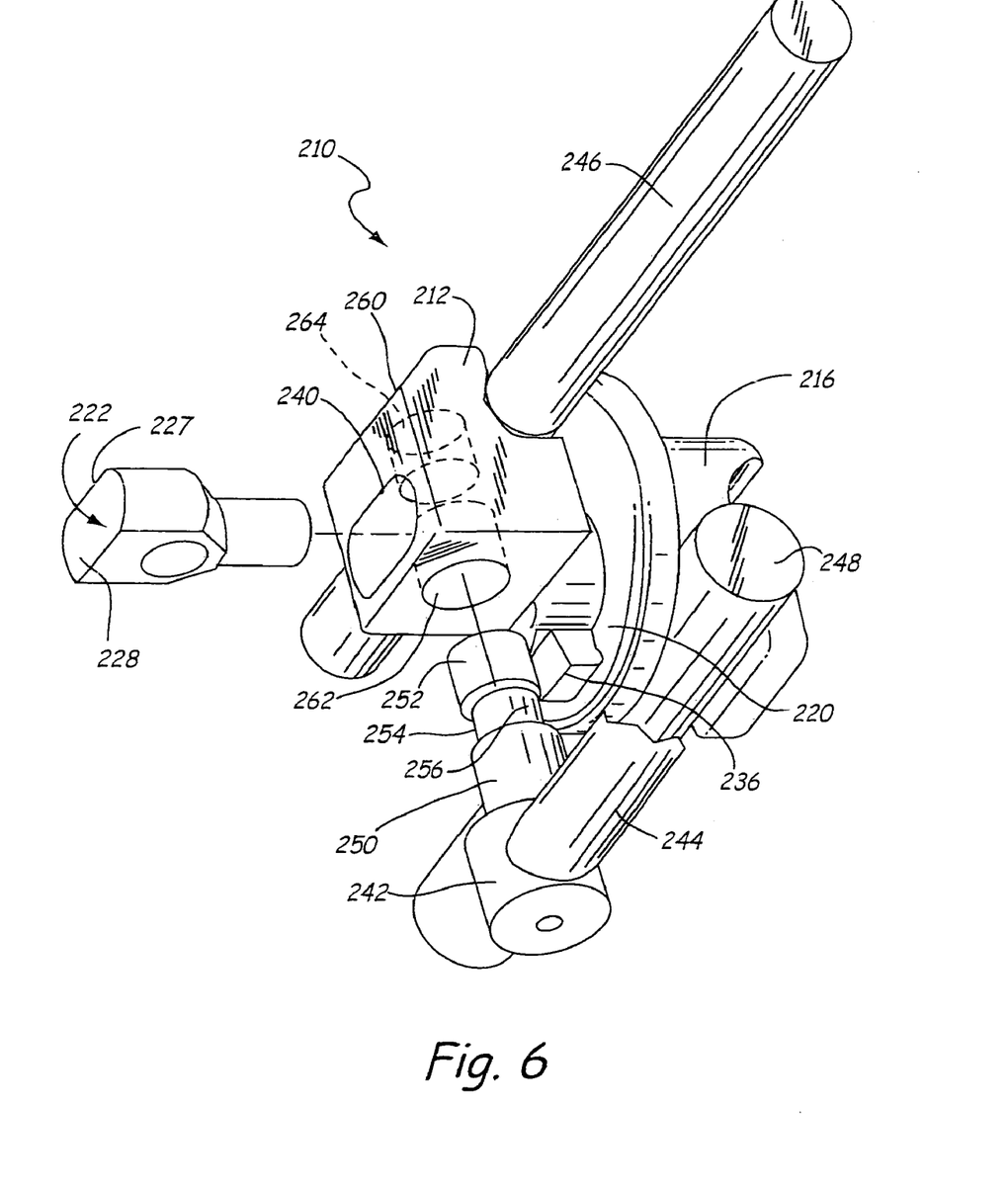
FIG. 6 is a partially exploded perspective view of the first alternative embodiment of the surgical clamp of the present invention.
Figure 7:
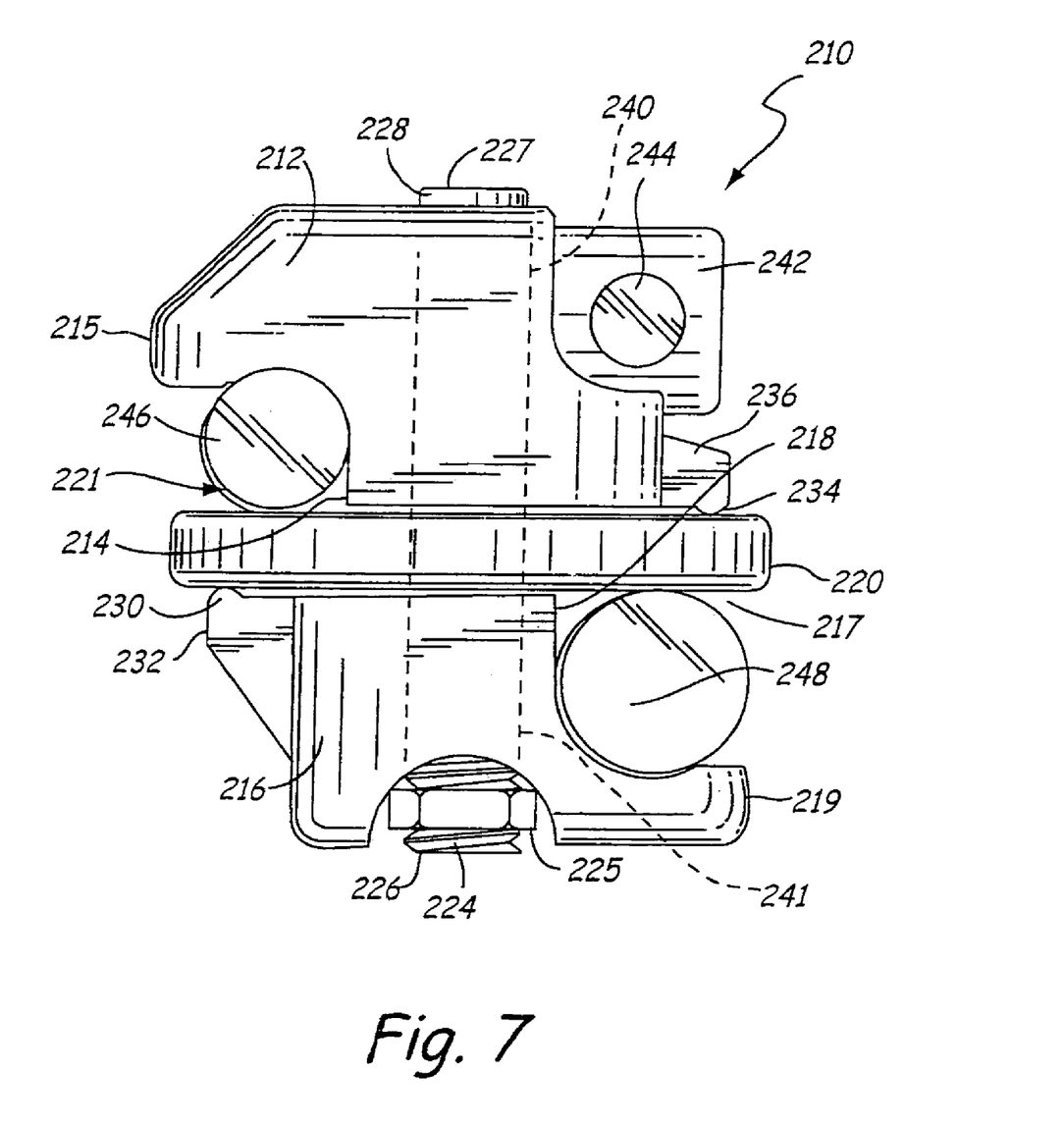
FIG. 7 is a side view of the first alternative embodiment of the surgical clamp of the present invention.

An alternative embodiment of the surgical clamp of the present invention is illustrated in FIGS. 6 and 7 at 210. The clamp 210 includes a first clamping member 212 and a second clamping member 216 separated by a washer 220. A shaft 222 is disposed through the first and second clamping members 212, 216, respectively. The shaft 222 includes an externally threaded portion 224 proximate a first end 226, a head 228 proximate a second end 227 and an intermediate portion (not shown) between the head 228 and the threaded portion 224.

The threaded portion 224 of the shaft 222 is disposed through an elongated bore 240 within the first clamping member 212 and through a bore 241 within the second clamping member 216. A nut 225 threadably engages the threaded portion 224 and retains the first and second clamping members 212, 216, respectively, about the shaft 222.

The first clamping member 212 is preferably made of a unitary structure having a surface 214 defining a first clamping slot 221 proximate a first end 215 and a first pivot surface 234 proximate a second end 236 which contacts an upper surface of the washer 220. The first clamping member 212 includes the elongated bore 240 for accepting the head 228 of the shaft 222.

The first clamping member 212 includes an integral collar 260 that cooperates with a camming pin 242. The camming pin 242 includes end portions 250, 252, respectively and an intermediate portion 254. The end portions 250, 252 and the intermediate portion 254 are generally cylindrical in shape and are located adjacent one to another. The end portions 250, 252 are centered about a rotational axis and are captivated within first and second through bores 262, 264, respectively. The captivated end portions 250, 252 rotatably support the intermediate portion 254 within the collar 260 and a through bore (not shown) within the head 228 of the shaft 222.

The shaft 222 is positioned through the elongated bore 240 within the first clamping member 212 including the integral collar 260 and the through bore 241 within the second clamping member 216, respectively, such that the head 228 is disposed within the elongated bore 240. The elongated bore 240 is elongated to allow the required movement of a head 228 of the shaft 222 when the clamp 210 is positioned from the first position to the second position and also in the reverse direction. The head 228 includes the through bore (not shown) that is aligned with the first and second through bores 262, 264, respectively, within the collar 260 and engages the intermediate portion 254 of the camming pin 242.

The intermediate portion 254 is eccentrically coupled between the end portions 250, 252, respectively. The intermediate portion 254 includes an outer circumferential surface 256 having an axis that is spaced from the rotational axis the camming pin 242 by a selected distance. The distance separating the axis of the camming pin 242 and the axis of the intermediate portion 256 generally determines the maximum distance that the camming pin 242 moves the shaft 222 relative to the first and second clamping members 212, 216, respectively. Preferably, the distance separating the axis of the camming pin 242 and the axis of the intermediate portion 254 is sufficient to frictionally secure first and second surgical rods 246, 248 within the first and second clamping members 212, 216, respectively.

The second clamping member 216 is also preferably a unitary structure having a surface 218 defining a second clamping slot 217 proximate a first end 219 and a second pivot surface 230 proximate a second end 232. The second pivot surface 230 contacts a bottom surface of the washer 220.

In operation, a handle 244, fixedly attached to the camming pin 242, is in a first position such that the first and second clamping slots 221, 217 of the first and second clamping members 212, 216 accept first and second support members 246, 248, all respectively. The movement of the handle 244 from the first position to a second position causes the intermediate portion 254 to engage the shaft 222. As the shaft 222 is engaged, a force is applied to the first clamping member 212.

The force causes the first clamping member 212 to pivot about the first pivot surface 234 such that the first support member 246 is frictionally engaged between the first clamping member 212 and the upper surface of the washer 220. The force is also applied to the second clamping member 216 and causes the second clamping member 216 to pivot about the second pivot surface 230 and causes the second support member 248 to be frictionally engaged between the bottom surface of the washer 220 and the second clamping member 216.

Thus, a simple actuation of the handle 244 and the camming pin 242 frictionally clamps the first and second support members 246, 248 within the first and second clamping members 212, 216, respectively, in selected rotational and axial positions. Conversely, the opposite movement of the handle 244 and rotation of the camming member 242 moves the head portion 228 of the shaft 222 relative to the first and second clamping members 212, 216 to reduce the forces that frictionally bind the first and second support members 246, 268 and thereby allow the first and second support members 246, 248 to be removed from the first and second clamping surfaces 214, 218, respectively.

The surgical clamp 210 enables a physician to quickly and easily adjust and re-adjust the rotational positions of the first and second clamping members 212, 216 as well as the position of the first and second support members 246, 248, respectively, within the first and second clamping members 212, 216 by providing a force perpendicular to an axis of the first and second surgical rods 246, 248. As a result, the surgeon can easily add an additional retractor where needed by disposing the clamp 210 about the second surgical rod 248 and providing a force perpendicular to an axis of the second support member 248 thereby disposing the second support member within the second clamping slot 217.

Further, the first support member 246, in this instance a retractor handle, is easily disposed within the first clamping slot 221 without having to dispose an end of the first support member 246 through the first clamping slot 221. By rotating the handle 244 and camming pin 242 between the first non-clamping position and the second clamping position, the clamp 210 frictionally engages the first surgical rod 246 and the second surgical rod 248. As a result, adding an additional retractor within a surgical site is simple, quick and does not require the surgical team to break down any of the apparatus surrounding the surgical site.

Figure 8:
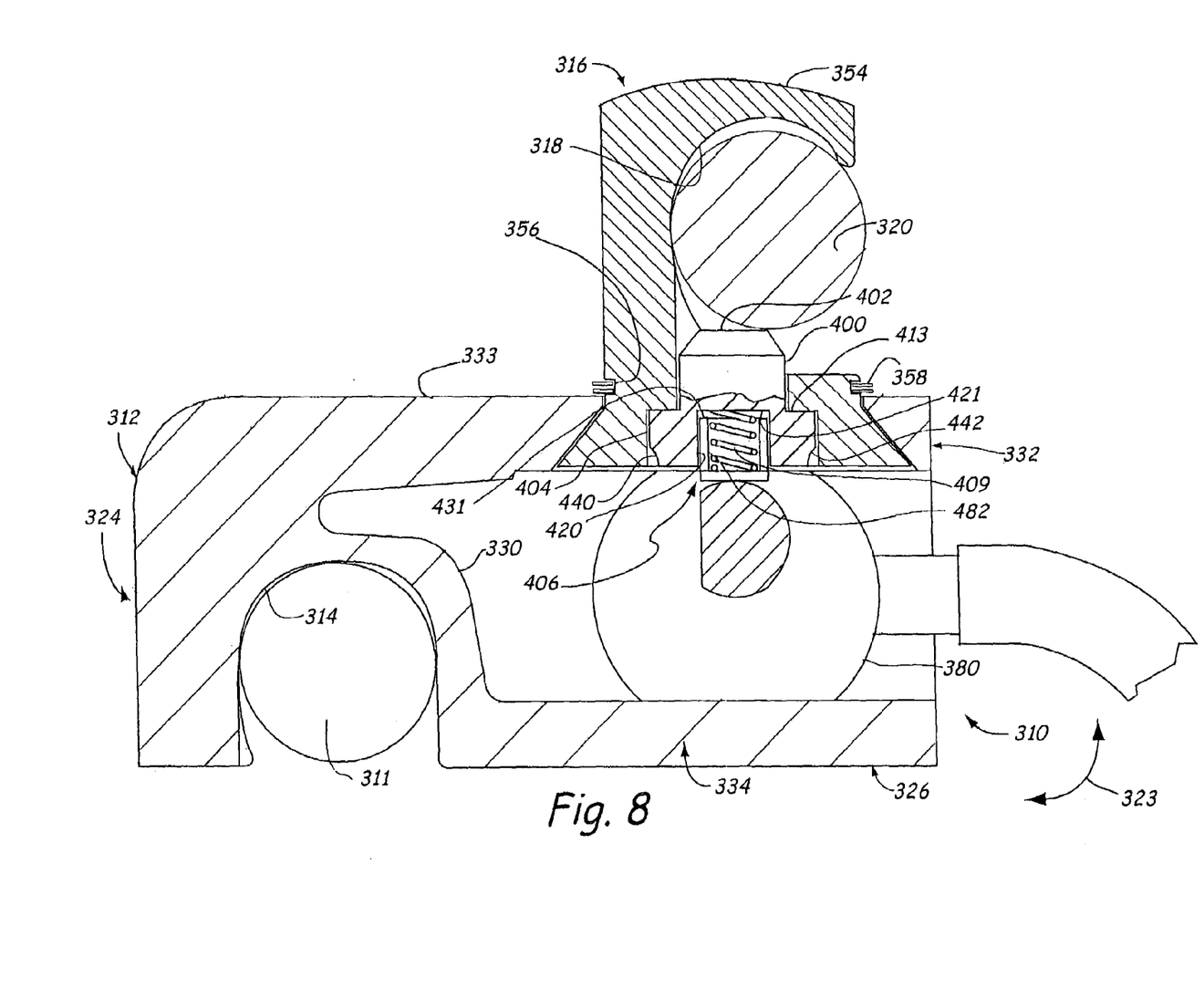
FIG. 8 is a sectional view of the second alternative embodiment of the surgical clamp of the present invention.

A second alternative embodiment of the surgical clamp of the present invention is generally illustrated in FIG. 8 at 310. The clamp 310 includes a first clamping member 312 having a first clamping surface 314 and a second clamping member 316 having a second clamping surface 318. Other components may be substituted for the second clamping member 316 such as, but not limited to, permanently attached retractors, or retractors that are attached using other types of clamps or fasteners.

To position the clamp 310 within the surgical site, a clamping end 324 of the first clamping member 312 is positioned proximate a retractor support arm 311. The first clamping surface 314 proximate the clamping end 324 is disposed about the portion of the retractor support arm 311 by applying manual force substantially perpendicular to an axis of the retractor support arm 311.

Figure 9:
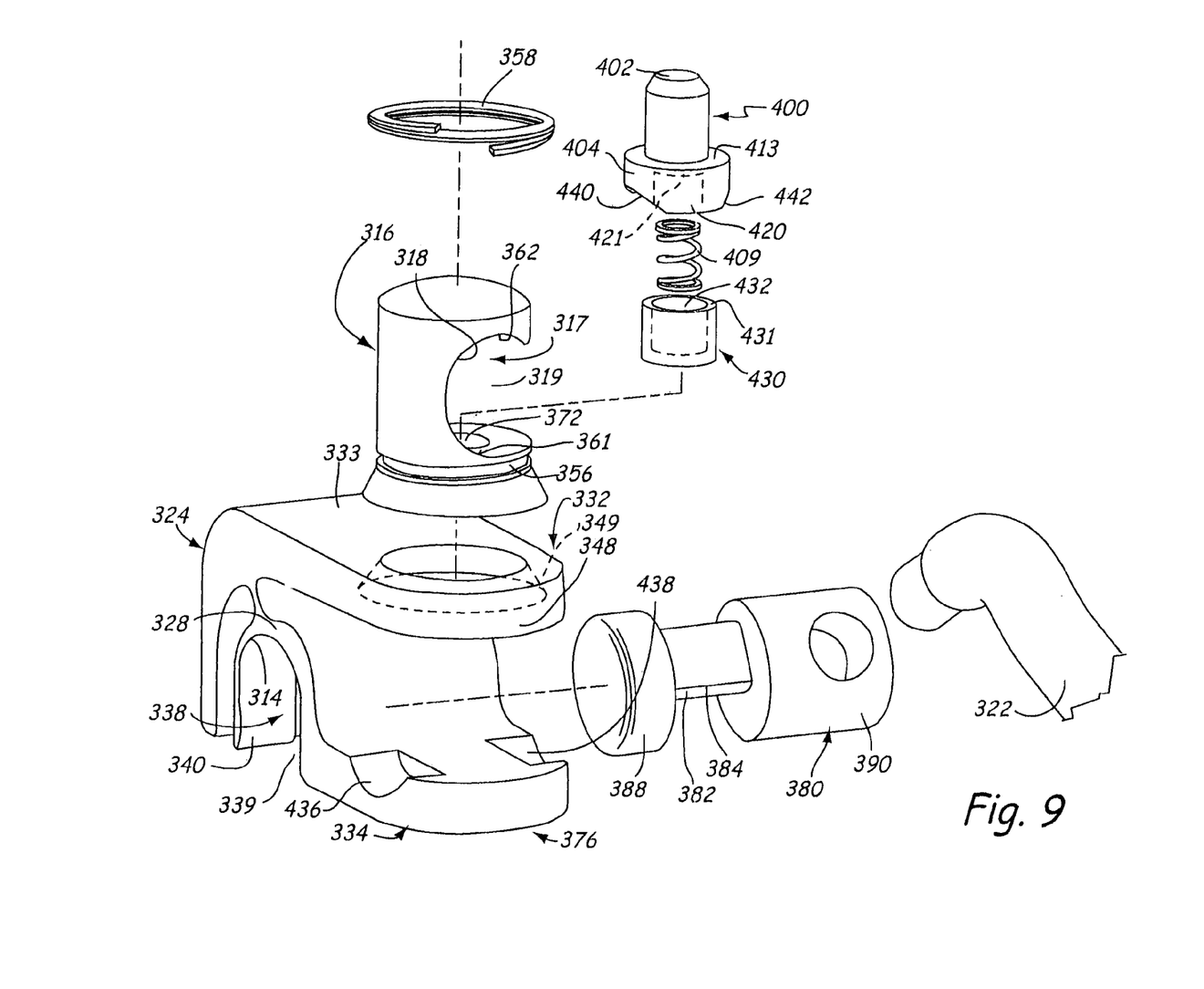
FIG. 9 is an exploded view of the second alternative embodiment of the surgical clamp of the present invention.

The first clamping member 312 also includes a fulcrum portion 328 proximate the clamping surface 314 and located between an upper leg portion 332 and a lower leg portion 334 as best illustrated in FIGS. 8 and 9. The fulcrum portion 328 allows the upper leg portion 332 to move with respect to the lower leg portion 334 so that the retractor support arm 311 may be clamped within the first clamping surface 314.

An actuating mechanism 380 is disposed within a recess 330 defined by the upper leg portion 332 and the lower leg portion 334 of the first clamping member 312 as illustrated in FIG. 8. The actuating mechanism 380 preferably is a camming pin.

The camming pin 380 is movable within the recess 330 and forces the upper and lower leg portions 332, 334 apart and causes the fulcrum portion 328 to flex. As the fulcrum portion 318 flexes, a clamping slot 338 defined by the first clamping surface 314 constricts such that the first clamping surface 314 frictionally engages the retractor support arm 311. The first clamping surface 314 is configured to generally conform to the cross-sectional configuration of the retractor support arm 311, but may be configured to conform to other shaped cross-sections.

Referring to FIGS. 8 and 9, the clamping slot 338 permits the first clamping member 312 to be placed on the retractor support arm 311 without moving any other surgical equipment that has been previously disposed upon the retractor support arm 311. When the clamp 310 is in a non-clamping position, the first clamping member 312 is retained upon the retractor support arm 311 by a constricted entrance 339 to the clamping slot 338. A bead or raised surface 340 is disposed substantially along a length of the clamping slot 338 to constrict the entrance 339.

The constricted entrance 339 provides a preliminary clamping force around the portion of the retractor support arm 311 such that the constricted entrance 339 to the clamping slot 338 prevents the clamp 310 from slipping off the retractor support arm 311 when the clamp 310 is in non-clamping position. The entrance 339 of the clamping slot 338 should not be so constricted to prevent use of manual force to position the first clamping member 312 about the portion of the retractor support arm 311. However, the entrance 339 of the clamping slot 338 should be sufficiently constricted to prevent the first clamping member 312 from accidentally slipping off of the retractor support arm 311.

The second clamping member 316 extends through a through bore 348 defined by a frusto-conical surface 349 within the upper leg portion 332 of the first clamping member 312. The second clamping member 316 includes a frusto-conical surface 350 at a proximal end 352 that cooperates with the frusto-conical surface 349 of the upper leg portion 332.

With the second clamping member 316 being positioned within the upper leg portion 332, an annular groove 356 on the second clamping member 316 is positioned above an upper surface 333 of the upper leg portion 332. A snap ring 358 is disposed within the annular groove 356 that rotatably captivates the second clamping member 316 within the upper leg portion 332 of the first clamping member 312 as illustrated in FIG. 8.

Referring to FIGS. 8 and 9, the second clamping surface 318 is positioned on a distal end portion 354. A retractor handle 320 is disposed proximate an entrance 319 to an opening 317 defined by the second clamping surface 318. Manual force is applied to the retractor handle 320 substantially perpendicularly to an axis to position the retractor handle 320 within the opening 317 by displacing an end 402 of a shaft 400 from the opening 317. The end 402 is positioned into the opening 317 through a through bore 372 extending through the second clamping member 316 along an axis 373 and intersects a bottom portion 361 of the clamping surface 318. With the end 402 displaced from the opening 317, the entrance 319 to the opening 317 is not constricted thereby allowing the retractor handle 320 to be disposed within the opening 317.

With the retractor handle 320 positioned within the opening 317, a compression spring 409, disposed between the shaft 400 and a spacer 30 that contacts the camming pin 380, biases the end 402 of the shaft 400 back into the opening 317. The end 402 and the arcuate upper portion 362 retain the retractor handle within the opening 317 such that the retractor handle is slidably positionable with respect to the second clamping surface 318.

The second clamping member 316 is positioned into a clamping position at approximately the same time that the camming pin 380 forces the first and second leg portions 332, 334 apart. When the second clamping member 316 is in the clamping position, the second clamping member 316 is non-rotatably fixed with respect to the first clamping member 312 and the retractor handle 320 is frictionally engaged within the second clamping surface 318.

The camming pin 380 is positionable between a first non-clamping position and a second clamping position. In the first non-clamping position the first and second clamping members 312, 316, respectively, are in a non-clamping position and the second clamping member 316 is rotatable within the first clamping member 312. In the second clamping position, the retractor support apparatus 311 is frictionally engaged with the first clamping surface 314 and a retractor support handle 320 is frictionally engaged between the arcuate upper portion 362 of the second clamping surface 318 and the end 402 of the shaft 400. Additionally, the second clamping member 316 is rotatably fixed with respect to the first clamping member 312 by a frictional engagement of the cooperating frusto-conical surfaces 349, 350.

The camming pin 380 is positioned within the recess 330 where the camming pin 380 includes a first cylindrical portion 388 and a second cylindrical portion 390 that are separated by the canning surface 382 which has an axis offset from the axis of rotation of the camming pin 380. Although a specific cam is described and illustrated in the drawings, other cam configurations are included within the present invention. By cam is meant an element having a raised surface or projecting part that when moved or rotated imparts an intermittent, alternate or variable motion.

The first and second cylindrical portions 388, 390, respectively, are rotatably positioned within first and second arcuate recesses 436, 438, respectively, within the lower leg portion 334 and first and second arcuate recesses 440, 442, respectively, within a lower portion 404 of the shaft 400. The first arcuate recesses 436, 440, respectively, cooperate to rotatably retain the first cylindrical portion 388 and the second arcuate recesses 438, 442, respectively, cooperate to rotatably retain the second cylindrical portion 390 such that the camming pin 380 is rotatable between the first and second positions.

With the camming pin 380 in the first position, the spacer 430 is positioned on a flat surface 384 of the camming pin 380. With the spacer 430 positioned on the flat surface 384, the compression spring 409 biases a shoulder 413 towards the proximal end 350 of the second clamping member 316 and biases the end 402 of the shaft 400 into the opening 317. A first end of the compression spring 409 is disposed within a cavity 420 of the shaft 400. A second end of the compression spring 409 is disposed within the cavity 432 within a spacer 430 where the spacer 430 is slidably positionable within the cavity 420.

As the camming pin 380 is rotated into the second position, the spacer 430 is positioned on and raised by the camming surface 382. As the spacer 430 is raised, the compression spring 409 compresses until an end 431 of the spacer 430 contacts a surface 421 within the cavity 420. With the surfaces 421, 431 contacting and the camming pin 380 in the second clamping position, the shoulder 413 is forced into the proximal end 352 of the second clamping member 316 creating a frictional engagement with the frusto-conical surfaces 349, 350. Additionally, the end 402 of the shaft 400 is forced into the opening 317 such that the retractor handle 320 is secured within the opening 317 by a frictional engagement between the end 402 of the shaft 400, the retractor handle 320 and the arcuate upper surface 362.

In operation, the camming pin 380 is positioned in the first position when the spacer 430 is positioned on the flat surface 384. With the camming pin 380 in the first position, the first clamping member 312 and the second clamping member 316 can accept the retractor support arm 311 and the retractor handle 320, respectively, and the second clamping member 316 is rotatable with respect to the first clamping member 312.

The first clamping member 312 is disposed in a selected position on the retractor support arm 311 by positioning the constricted entrance 339 of the clamping slot 338 proximate the retractor support arm 311. Manual force is applied to the first clamping member 312 substantially perpendicular to an axis of the retractor support arm 311 to overcome the constricted entrance 339 of the clamping slot 338, thereby disposing the first clamping member 312 about the retractor support arm 311. With the canning pin 380 in the first position, the first clamping member 312 is slidably positionable on the retractor support arm 31.

With the first clamping member 312 positioned on the retractor support arm 311, the retractor handle 320 is positioned proximate the constricted entrance 319 of the opening 317 within the second clamping member 316. Manual force is applied substantially perpendicular to an axis of the retractor handle 320 to force the end 402 of the shaft 400 from the opening 317 and position the retractor handle 320 within the opening 317. With the retractor handle 320 positioned within the opening 317, the compression spring 409 biases the end 402 of the shaft 400 into the opening 317 such that the retractor handle 320 is slidably retained within the second clamping surface 318.

To position the camming pin 380 into the second or clamping position, a handle 322 fixedly attached to the camming pin 380 is moved in the direction of arrows 323 as illustrated in FIG. 8, which rotates the camming pin 380 about the first and second cylindrical portions 388, 390, respectively. As the camming pin 380 is rotated about the first and second cylindrical portions 388, 390, the spacer 430 is raised into the cavity 420 and compresses the compression spring 409. A maximum force is placed upon the spacer 430 and shaft 400 when the camming pin 380 is positioned into the second position when the end 431 of the spacer 430 contacts the surface 421 within the cavity 420 and applies the force to the shaft 400.

Referring to FIG. 8, with the camming pin 380 in the second clamping position, a distance between the spacer 430 and the lower leg portion 334 is less than the distance between portions of the cylindrical portions 388, 390 within the arcuate recesses 436, 438, respectively, and an upper edge of the camming surface 382 thereby forcing the first and second leg portions 332, 334 apart. With the first and second leg portions 332, 334 forced apart, the fulcrum portion 328 flexes which causes the first clamping slot 338 to constrict such that the first clamping surface 314 frictionally engages the retractor support arm 311.

With the camming pin 380 in the second position, the shoulder 413 is forced into the proximal end 352 of the second clamping member 316 and creates a frictional engagement between the cooperating frusto-conical surface 349 of the through bore 348 in the upper leg portion 332 and the frusto-conical surface 350 of the second clamping member 316. The frictional engagement of the frusto-conical surfaces 349, 350 prevents rotational movement of the second clamping member 316 with respect to the first clamping member 312.

With the camming pin 380 in the second position, the first end 402 of the shaft 400 is raised into the opening 417 through the through bore 372. The raised first end 402 of the shaft 400 contacts the retractor handle 320 and creates a frictional engagement between the arcuate upper portion 362 of the second clamping surface 318, the retractor handle 320 and the first end 402 of the shaft 400.

The retractor clamp 310 can be repositioned on the support arm 311 by first positioning the camming pin 380 into the first position such that the first clamping slot 338 is not constricted and detaching the first clamping member 312 from the retractor support arm 311. The first clamping member 312 is detachable from the retractor support arm 311 by applying manual force in an opposite direction as used to position the first clamping member 312 on the support arm 311. After the clamp 310 has been removed from the retractor support arm 311, the clamp 310 is repositionable on the retractor support arm 311 by positioning an entrance 339 to the clamping slot 338 against the retractor support arm 311 and applying manual force substantially perpendicular to the axis of that portion of the retractor support arm 311.

The retractor handle 320 can also be repositioned within the second clamping member 316 without having to slide the retractor handle 320 with respect to the second clamping surface 318. The retractor handle 320 is removed from the second clamping member 316 by providing manual force in the opposite direction of the force used to position the retractor handle 320 within the opening 317 of the second clamping member 316. The retractor handle 320 can be reinserted into the opening 317 by reapplying manual force generally perpendicular to the axis of the retractor handle 320.

Although the present invention has been described with reference to preferred embodiments, workers skilled in the art will recognize that changes may be made in form and detail without departing from the spirit and scope of the invention.

What is claimed is:

1. A surgical joint comprising:
    a first clamping member comprising a first clamping surface for engaging a first surgical rod and an attachment end;
    a second clamping member mounted with respect to the first clamping member wherein the second clamping member comprises a second clamping surface for engaging a second surgical rod;
    a shaft disposed through and positioned within the attachment end of the first clamping member and wherein the shaft is in communication with the second clamping member; and
    a camming mechanism having a handle fixedly attached thereto and wherein the camming mechanism directly contacts an external surface of the handle and wherein the camming mechanism is disposed between the first and second clamping members and disposed about the shaft wherein when the camming mechanism and the shaft are movable with respect to each other to position the first and second clamping members in either a non-clamping position or a clamping position by gripping and applying a manual force to the handle.

2. A low profile surgical clamp mounted to a retractor support apparatus comprising:
    a first clamping member for engaging the retractor support apparatus and an attachment end;
    a second clamping member for engaging a retractor and being mounted with respect to the first clamping member;
    a shaft extending through the attachment end of the first clamping member;
    an actuating mechanism having a camming surface engaging the shaft and positioned between the first and second clamping members wherein the actuating mechanism is movable to position the first and second clamping members between a nonclamping position and a clamping position; and
    a handle fixedly connected to the actuating mechanism and wherein the actuating mechanism directly contacts an external surface of the handle.

3. A surgical clamp for clamping surgical devices, the clamp comprising:
    a clamping member with a clamping cavity;
    a pin extending through the clamping member and into the clamping cavity; and
    a camming mechanism that moves the pin within the cavity placing the clamping member in a clamping position.

4. The surgical clamp of claim 3 and further comprising a spring that biases the pin into the clamping cavity.

* * * * *